United States Patent [19]

Girard

[11] 4,427,692

[45] Jan. 24, 1984

[54] AGGLOMERATED HALO-HYDANTOINS

[75] Inventor: Theodore A. Girard, Williamsport, Pa.

[73] Assignee: Glyco, Inc., Williamsport, Pa.

[21] Appl. No.: 481,018

[22] Filed: Apr. 6, 1983

Related U.S. Application Data

[63] Continuation of Ser. No. 331,062, Dec. 15, 1981, abandoned.

[51] Int. Cl.³ ............................................. A01N 43/50
[52] U.S. Cl. ................................................ 424/273 R
[58] Field of Search ......................................... 424/273

[56] References Cited

U.S. PATENT DOCUMENTS 3,412,021 11/1968 Paterson ............................. 424/273
4,297,224 10/1981 Macchiarold et al. ............. 210/755

Primary Examiner—Elbert L. Roberts
Attorney, Agent, or Firm—Cushman, Darby & Cushman

[57] ABSTRACT

Spherical agglomerates of dihalodimethylhydantoins and dimethylhydantoins are prepared by feeding a mixture of the hydantoins together to the surface of an agglomerating disc in conjunction with a spray of water, and subsequently drying the agglomerates. These agglomerates possess a hard structural integrity and exhibit a uniform and controlled dissolution when placed in an aqueous environment, thereby rendering them suitable for a variety of applications including automatic dishwashing detergents, industrial bleaches, as well as disinfectants for cooling towers, swimming pools and spa waters.

13 Claims, No Drawings

AGGLOMERATED HALO-HYDANTOINS

This is a continuation, of application Ser. No. 331,062, filed Dec. 15, 1981 now abandoned.

BACKGROUND OF THE INVENTION

For many years, halogenated hydantoins have been employed in aqueous systems for a variety of applications. To a large extent, the halogenated hydantoins have been utilized for bleaching purposes as described, for example, in U.S. Pat. Nos. 4,078,099; 3,575,865; 3,481,878; 3,406,116 and 2,921,911.

Halogenated hydantoins have also been known to be effective for scouring, cleansing and disinfecting applications as illustrated by U.S. Pat. Nos. 2,789,078; 3,702,826 and 3,583,922.

Automatic dishwashing compositions of halogenated hydantoins are also well known as taught for example by U.S. Pat. No. 4,102,799.

The treatment of cooling tower waters, swimming pools and the like systems with halogenated hydantoins is illustrated in U.S. Pat. Nos. 4,297,224 and 3,412,021.

In many of these applications, it has been desirable to utilize the halogenated hydantoins in an agglomerated form as described in the aforementioned U.S. Pat. No. 3,412,021 so as to control the release of the halohydantoin.

Known methods of agglomerating halohydantoins generally involve conventional pelletizing or briquetting operations which may require use of binders or sticking agents. It has also been proposed to use compacting rolls to fabricate the halohydantoins into various forms.

These current methods are severely hindered by the very dusty and corrosive nature of the halogenated hydantoins, which has contributed to high maintenance costs for equipment and unsatisfactory work environments. Furthermore, the halogenated hydantoins are susceptible to decomposition due to conditions of high humidity or excessive temperatures generated during processing in these procedures. Any acidic by-products of the decomposition could corrode metal surfaces, contaminate the product, and catalyze further decomposition.

Agglomerating discs (often referred to as "disc pelletizers") have developed in the art of "balling" in an attempt to eliminate dusting problems. While agglomerating discs are employed for a variety of industrial applications, no means has been provided heretofore for using such equipment in the agglomeration of halohydantoins.

It is therefore a primary object of the present invention to provide a method for agglomerating halogenated hydantoins into a spherical form having a hard structural integrity.

A further object of the present invention is to provide spherical agglomerates of halogenated hydantoins which, when placed in water, retain their shape and integrity for periods of time sufficient to provide a uniform and controlled release of the active halogen.

Still a further object of the present invention is to provide an improved means for the disinfecting of recirculating aqueous systems through the controlled release of active halogen.

These and other objects of the invention will become more apparent from the discussion which follows.

DETAILED DESCRIPTION OF THE INVENTION

In accordance with the present invention there is provided a means of forming spherical agglomerates of a dihalogenated hydantoin by feeding a mixture of 5,5-dimethylhydantoin (DMH) and N,N'-dihalo-5,5-dimethylhydantoins to the surface of a rotating agglomerating disc and concurrently spraying the mixture on the disc with water to form spherical agglomerates having a water content of 30% or less. The resulting agglomerates are then dried thereby resulting in a hard sphere of excellent physical integrity.

The halogenated hydantoin and DMH may be conveniently fed to the disc surface in a variety of forms and separately or in combination. It is preferred, however, to form a dry pre-mix of the DMH and halogenated hydantoin which is fed to the disc surface and sprayed concurrently on the surface with water to the desired level. Alternatively, one may feed the hydantoin materials, singly or in combination, in an aqueous or moist state. Thus, one may dissolve DMH in the water which is sprayed upon the disc surface, since DMH is soluble to some extent in water. One may increase the temperature of the water in order to achieve the desired level of DMH solubility. Also, as the halogenated hydantoins when prepared are generally precipitated in an aqueous solution, one can feed the material in such a moistened state directly to the disc.

Agglomerating discs which may be used in accordance with the present invention are well known in the art and are readily available from various manufacturers. These discs are characterized by a flat surface having baffles positioned above surface and a rim circumscribing the edge thereof. The disc rotates at an appropriate angle to the horizontal. Generally an angle of from about 40° to 60° is employed and preferably about 45°, but such is not critical.

The art of "balling" or agglomerating is known as is the equipment required as noted in "The Theory and Practice of Disc Balling" by S. B. Floyd, Jr. and W. H. Engelleitner, IBA Proceedings, Vol. 10, pp. 51–58 (1967), and "Disc Pelletizing Theory and Practice" by Carl A. Holley, Ferro-Tech Form 149, pp. 1–8 (Copyright 1979). There are a number of factors which influence formation of the agglomerates to produce a wide range of product sizings from the disc from the feed. The angle of the disc to the horizontal, speed of the disc, point of feed application and location of the water spray(s) each influence the sizing, but the primary factors are the feed position and location of the water sprays. Thus, for a relatively small (i.e., about 3/16 inch diameter) pellet the feed may be placed at approximately the 3 o'clock position on the disc with a water source above and in line with the feed point. Initial pellet growth takes places in the outer stream of the disc. Larger products result from a change in position of the feed progressively from the right to left-hand side (discharge side) of the disc with a primary water source above the feed point, e.g., at 10 or 11 o'clock on the disc. The baffles positioned above the disc surface affect the stream flow of particles and resulting agglomerates. As for the disc speed, this may vary widely with most discs having pre-set speeds. Generally, from 3 to 60 rpm may be used, and preferably about 10 to 25 rpm, but this is not critical.

There are a number of halogenated hydantoins which may be used, but preferably the active material is selected from the group consisting of N,N'-dichloro-5,5-dimethylhydantoin, N-bromo-N'-chloro-5,5-dimethylhydantoin and N,N'-dibromo-5,5-dimethylhydantoin, with the N-bromo-N'-chloro-5,5-dimethylhydantoin being most preferred.

A surprising feature of the present invention is the enhanced structural integrity which the addition of dimethylhydantoin to the halogenated hydantoin provides to the resulting spherical agglomerate. In the absence of the 5,5-dimethylhydantoin (DMH) the halogenated hydantoin when fed to the disc with water results in a friable agglomerate having no substantial integrity and which readily crumbles when pressed. However, with the addition of DMH one obtains a relatively hard spherical agglomerate having excellent structural integrity (i.e. it does not dust or flake, and maintains its shape when dropped or mechanically mixed with other materials).

The spherical agglomerates of the present invention may be formed in a wide range of diameters depending upon the feed rate of hydantoins to the disc, speed of the disc and angle of the disc and other factors noted above. These parameters are all within the capability of one familiar with the operation of agglomerating discs and are not critical to the invention claimed herein. Generally, agglomerates ranging from about 3/16 of an inch to about one inch (and preferably about 0.75 inch) are suitable. It will be appreciated that the size of agglomerates formed will depend upon the use desired. Thus, smaller agglomerates may be more well suited to bleach and scouring compositions, whereas larger agglomerates may be best for use in swimming pools and spas.

The amount of DMH and dihalogenated hydantoin which are fed to the disc may vary considerably. However, generally from about 70 to 95 parts by weight (preferably about 90 parts) of the dihalogenated dimethylhydantoin is mixed with from about 5 to about 30 parts by weight (preferably about 10 parts) of the DMH. These materials preferably are pre-mixed in granular or powder form and then fed to the rotating disc and sprayed with a sufficient amount of water to provide a moisture content of 30% or less (preferably from about 15 to 25%, and most suitably about 20%).

The following examples are offered to more fully illustrate the present invention, but are not to be constured as limiting the scope thereof.

EXAMPLE ONE

Ninety parts by weight of powdered N-bromo-N'-chloro-5,5-dimethylhydantoin (BCDMH) were mixed with ten parts by weight of DMH and fed to an agglomerating disc (Sprout Waldron—39 inch diameter Model 1000) at a nominal feed rate of 400 lbs./hour. The speed setting of the disc was 3 (10 to 15 rpm) and the feed angle 45°. The feed mixture was sprayed with water which was introduced at the rate of 100 lbs./hour. The resulting spherical agglomerates were approximately 0.5 inch in diameter and were dried in a convection drier at 65° C.

These agglomerates were hard and maintained their shape when handled with no dusting or flaking. When placed in water, the agglomerates provided a uniform and steady release of active halogen.

EXAMPLE TWO

A series of agglomerates using a variety of feeds were prepared using a Sprout-Waldron 16-inch agglomerating disc at an angle of 45° C. and constant speed. The moisture content and properties of the resulting agglomerated balls are set forth in Table 1 below.

TABLE 1

| Feed Material | % Moisture | Physical Properties |
|---|---|---|
| BCDMH | 27.0 | Crumbled and dusty - no integrity |
| BCDMH | 28.3 | Crumbled and dusty - no integrity |
| BCDMH | 23.4 | Crumbled and dusty - no integrity |
| BCDMH | 25.0 | Crumbled and dusty - no integrity |
| BCDMH | 26.1 | Crumbled and dusty - no integrity |
| BCDMH | 25.6 | Crumbled and dusty - no integrity |
| BCDMH | 25.4 | Crumbled and dusty - no integrity |
| BCDMH | 25.4 | Crumbled and dusty - no integrity |
| BCDMH + 2.9% DMH | 25.8 | Friable and crumbly |
| BCDMH + 1.4% DMH | 25.9 | " |
| BCDMH + 10% DMH | 25.5 | Hard pellet with structural integrity |
| BCDMH + 10% DMH | 25.1 | Hard pellet with structural integrity |
| BCDMH + 5% DMH | 27.1 | Pellet with dusting and slight integrity |

EXAMPLE THREE

The effect of adding DMH to BCDMH on the quality of an agglomerated pellet was investigated by both dry blending DMH with the BCDMH fed as well as adding the DMH together with the water spray using the agglomerating disc of Example Two. The disc speed was set at 2, at an angle of 45° with a nominal feed rate of 45 lb/hour BCDMH and a nominal water rate of 12.5 lb/hour. The resulting particles were then tested for crushing strength and product abrasion loss according to the following procedures and the results are set forth in Table 2 below.

Crush Test

Nonselective (Grab Sample)

1. A small grab sample of 30 particles or so is placed on the pan of a top loading balance (Sartorius, Type 2251).

2. Five samples, selected at random, are crushed on the pan with the head of a 7/16 in. stove bolt.

3. The weight in grams indicated on the balance immediately before the particle is crushed is recorded as the crushing strength of that particle.

4. The average of the five particles, expressed in grams, is referred to as the crushing strength of the sample.

Selective (Screened Sample)

1. A sample of sufficient volume is screened through a series of sieves in order to obtain ten or more particles of a desired mesh size.

2. Steps 2 through 4 above are repeated.

Abrasion Test

1. A representative sample for 30 grams is screened by hand through a series of sieves of decreasing mesh size (i.e., 8, 10, 12, 14, 20, 35, 48, 100, 200).

2. Each portion that is collected on the various sieves is carefully weighed and expressed as a percentage of the total sample sieved.

3. The largest percentage collected on the various sieves determines the "largest sieve fraction." The range of sieves on which portions were collected, in addition to the largest sieve fraction, is used to characterize the particle size distribution of the sample.

4. 10 grams of the largest sieve fraction is placed on the next smaller sieve and screened for 5 minutes using an automatic shaker (Fritch, Analysette) set on the highest amplitude (10).

5. The fraction that passes through the sieve is carefully weighed, expressed as a percent, and recorded as "abrasion loss."

TABLE 2
Effect of Added DMH on BCDMH Quality

| | |
|---|---|
| Disc Speed: | 2.0 Set. |
| Disc Angle: | 50° |
| Nominal Feed Rate: | 45 lb/hr. dry BCDMH |
| Nominal Water Rate: | 12.5 lb/hr. |

| Run No. | DMH Added Via | Calculated Wt. % DMH in Dry BCDMH Product | Crushing Strength, Grams[1] | Product Abrasion[2] Loss |
|---|---|---|---|---|
| 1 | — | 0 | 38 | 36.3 |
| 2 | Water Spray | 1.4 | 42 | 19.3 |
| 3 | Water Spray | 2.9 | 45 | 14.8 |
| 4 | Dry Blend | 5 | 74 | 15.3 |
| 5 | Dry Blend | 10 | 101 | 1.9 |

[1]Hardness run on 14-20 mesh product fraction.
[2]Fritch-Analysette Automatic Sieve Shaker - Koppers procedure.

EXAMPLE FOUR

Tests were conducted to compare the release of halogen using agglomerates (about 0.5 inch diameter) of Example One with commercially available stick agglomerates (1"×3") of BCDMH such as described in U.S. Pat. No. 3,412,021. In these tests, 88 grams of each of the agglomerates were placed in a glass vessel with glass wool positioned above and below the agglomerates. The glass vessels were fitted with an overflow tube for collecting the samples at various time intervals. Tap water having a pH of 8.1 was introduced through the top of the vessel via a glass tube which extended to the bottom of the vessel and fed at a rate of 18 g/minute. The total and free halogen was measured and is expressed as active $Cl^+$ in ppm in Table 3 below.

TABLE 3
Active halogen expressed as $Cl^+$ in ppm

| Elapsed Time (Hrs) | Unit #1 Example One Total | Free | Unit #2 Commercial Sticks Total | Free |
|---|---|---|---|---|
| 1 | | | | |
| 2 | 237 | — | 103 | — |
| 3 | 259 | — | 75 | — |
| 5 | — | 73 | — | 15 |
| 10 | 177 | 85 | 54 | 17 |
| 17 | | | | |
| 22 | 138 | 70 | 28 | 13 |
| 30 | 133 | 56 | 25 | 8 |
| 64 | 94 | 44 | 16 | 6 |
| 71 | 90 | 44 | 16 | 5 |
| 88 | 73 | 38 | 16 | 7 |

From the foregoing examples, it will be appreciated that the agglomerates of the present invention provide for an improved means whereby one may disinfect recirculating aqueous systems such as cooling towers, air conditioners, swimming pools, spas and similar type environments. Treatment of such systems by contacting the water contained therein with a biocidally effective amount of the agglomerate results in a controlled release of active halogen to rid and/or keep the system free from undesirable microbial infestation. Generally from 1 to 2 ppm or greater of active halogen in the system is sufficient to disinfect and maintain the system free of infestation.

The invention having been thus described, it will be appreciated that various modifications may be made thereto without departing from the scope of the claims which follow. Furthermore, the materials and procedures of the present invention may comprise, consist or consist essentially of the hereinabove recited materials and procedures.

I claim:

1. In a process for the formation of spherical agglomerates which comprises feeding a finely divided material to an agglomerating disc which is characterized as a flat, disc having baffles positioned above the surface thereof and a rim circumscribing the edge thereof, the improvement which comprises feeding a mixture of 5,5-dimethylhydantoin and a dihalodimethylhydantoin together with a spray of water to the surface of said disc in a rotating state so as to form spherical agglomerates of the mixture having to a moisture content of 30% or less, and thereafter drying the spherical agglomerates.

2. The process of claim 1, wherein said dihalodimethylhydantoin is selected from the group consisting of N,N-dichloro-5,5-dimethylhydantoin, N-bromo-N'-chloro-5,5-dimethylhydantoin and N,N'-dibromo-5,5-dimethylhydantoin.

3. The process of claim 2, wherein said dihalodimethylhydantoin is N-bromo-N'-chloro-5,5-dimethylhydantoin.

4. The process of claim 1, 2 or 3 wherein the mixture contains from about 70 to 95 parts by weight of dihalodimethylhydantoin and from about 5 to 30 parts by weight of 5,5-dimethylhydantoin.

5. The process of claim 4 wherein the amount of water added to the spherical agglomerate ranges from about 15 to 25% by weight.

6. The process of claim 1 wherein the mixture contains about 90 parts by weight of N-bromo-N'-chloro-5,5-dimethylhydantoin, and about 10 parts by weight of 5,5-dimethylhydantoin.

7. The process of claim 1, 2, 3 or 6 wherein the diameter of the spherical agglomerate is from about 3/16 inch to about one inch.

8. The process of claim 7 wherein the diameter of the spherical agglomerate is about 0.75 inch.

9. The process of claim 1 wherein the 5,5-dimethylhydantoin fed to the surface of the disc is dissolved in the spray of water.

10. A spherical agglomerate having structural integrity and produced in accordance with the method of claim 6.

11. An improved method for the disinfection of a recirculating aqueous system through the controlled release of active halogen which comprises contacting water contained in said system with a biocidally effective amount of the agglomerate of claim 10.

12. The method of claim 11 wherein the amount of agglomerate is sufficient to provide at least 1 part per million of active halogen in said system.

13. The method of claim 12 wherein said system is a cooling tower, air conditioner, swimming pool or spa.

* * * * *